United States Patent
Oku et al.

(10) Patent No.: US 6,600,054 B2
(45) Date of Patent: Jul. 29, 2003

(54) PROCESS FOR PRODUCING PROPYLENE OXIDE

(75) Inventors: Noriaki Oku, Ichihara (JP); Toshikazu Omae, Kisarazu (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/221,366

(22) PCT Filed: Mar. 19, 2001

(86) PCT No.: PCT/JP01/02191

§ 371 (c)(1),
(2), (4) Date: Sep. 12, 2002

(87) PCT Pub. No.: WO01/70715

PCT Pub. Date: Sep. 27, 2001

(65) Prior Publication Data

US 2003/0023102 A1 Jan. 30, 2003

(30) Foreign Application Priority Data

Mar. 24, 2000 (JP) .................................... 2000-083959

(51) Int. Cl.[7] .............................................. C07D 301/19
(52) U.S. Cl. ...................................... 549/529; 549/523
(58) Field of Search .................................. 549/529, 523

(56) References Cited

U.S. PATENT DOCUMENTS

| | | |
|---|---|---|
| 3,350,422 A | 10/1967 | Kollar |
| 4,891,437 A | 1/1990 | Marquis et al. |
| 5,319,114 A | 6/1994 | Gaffney et al. |
| 5,410,077 A | 4/1995 | Wu et al. |
| 5,760,253 A | 6/1998 | Danner et al. |
| 5,840,933 A | 11/1998 | Jubin, Jr. et al. |

*Primary Examiner*—Ba K. Trinh
(74) *Attorney, Agent, or Firm*—Sughrue Mion, PLLC

(57) ABSTRACT

A process for producing propylene oxide, which comprises steps described below, wherein isopropylbenzene hydroperoxide supplied to an epoxidation step has not undergone a heat history including heating at a temperature not lower than the temperature ($t°$ C.) represented by the following equation (1), $$t(°C.)=150-0.8\times W \quad (1)$$

W: content (% by weight) of isopropylbenzene hydroperoxide in a solution containing isopropylbenzene hydroperoxide:

oxidation step; a step in which isopropylbenzene is oxidized to obtain isopropylbenzene hydroperoxide, epoxidation step; a step in which isopropylbenzene hydroperoxide obtained in the oxidation step is reacted with propylene to obtain propylene oxide and cumyl alcohol, and hydrogenolysis step; a step in which cumyl alcohol obtained in the epoxidation step is subjected to hydrogenolysis to obtain isopropylbenzene, and said isopropylbenzene is recycled to the oxidation step as a raw material for the oxidation step.

2 Claims, No Drawings

PROCESS FOR PRODUCING PROPYLENE OXIDE

This application is a 371 of PCT/JP01/02198, dated Mar. 19, 2001.

TECHNICAL FIELD

The present invention relates to a process for producing propylene oxide. More particularly, the invention relates to a process for producing propylene oxide, wherein said process for producing propylene oxide has excellent characteristics that propylene is converted to propylene oxide using isopropylbenzene hydroperoxide obtained from isopropylbenzene, as an oxygen carrier, that said isopropylbenzene can be repeatedly used, and that an activity of a catalyst used for epoxidation to obtain propylene oxide from propylene, can be maintained at a high level for long time.

BACKGROUND ART

A process in which propylene is oxidized using ethylbenzene hydroperoxide as an oxygen carrier to give propylene oxide and styrene is known as Halcon process. Since, in this process, styrene is inevitably produced together with propylene oxide, it is unsatisfactory from the viewpoint that only propylene oxide is to be selectively produced.

On the other hand, a concept of a process in which propylene is converted to propylene oxide using isopropylbenzene hydroperoxide obtained from isopropylbenzene, as an oxygen carrier, and said isopropylbenzene is repeatedly used, is described in Czechoslovak Patent No. CS 140,743. The process described in said patent does not contain precise descriptions concerning necessary steps except an oxidation step, epoxidation step and hydrogenolysis step. Various problems arise in practical recycling of isopropylbenzene and therefore the patent cannot be said as sufficient for industrial realization.

DISCLOSURE OF THE INVENTION

Under such circumstances, an object of the present invention is to provide a process for producing propylene oxide, wherein said process for producing propylene oxide has excellent characteristics that propylene is converted to propylene oxide using isopropylbenzene hydroperoxide obtained from isopropylbenzene, as an oxygen carrier, that said isopropylbenzene can be repeatedly used, and that an activity of a catalyst used for epoxidation to obtain propylene oxide from propylene, can be maintained at a high level for long time.

Namely, the invention relates to a process for producing propylene oxide, which comprises steps described below, wherein isopropylbenzene hydroperoxide supplied to an epoxidation step has not undergone a heat history including heating at a temperature not lower than the temperature ($t°$ C.) represented by the following equation (1), $$t(° C.)=150-0.8 \times W \quad (1)$$

W: content (% by weight) of isopropylbenzene hydroperoxide in a solution containing isopropylbenzene hydroperoxide:

oxidation step; a step in which isopropylbenzene is oxidized to obtain isopropylbenzene hydroperoxide, epoxidation step; a step in which isopropylbenzene hydroperoxide obtained in the oxidation step is reacted with propylene to obtain propylene oxide and cumyl alcohol, and hydrogenolysis step; a step in which cumyl alcohol obtained in the epoxidation step is subjected to hydrogenolysis to obtain isopropylbenzene, and said isopropylbenzene is recycled to the oxidation step as a raw material for the oxidation step.

BEST MODE FOR CARRYING OUT THE INVENTION

The oxidation step in the present invention is a step in which isopropylbenzene is oxidized to obtain isopropylbenzene hydroperoxide. The oxidation of isopropylbenzene is usually effected by autoxidation with oxygen-containing gas such as the air, an oxygen-enriched air or the like. The oxidation reaction may be carried out without any additive or with an additive such as an alkali. The reaction temperature is usually 50° C. or higher and lower than 150° C., and the reaction pressure is usually between the atmospheric pressure and 5 MPa. In the oxidation with an additive, the alkali includes alkali metal compounds such as NaOH, KOH and aqueous solutions thereof; alkaline earth metal compounds, alkali metal carbonates such as $Na_2CO_3$, $NaHCO_3$, ammonia, $(NH_4)_2CO_3$, alkali metal ammonium carbonates and the like and aqueous solutions thereof.

The epoxidation step in the present invention is a step in which isopropylbenzene hydroperoxide obtained in the oxidation step is reacted with propylene to obtain propylene oxide and cumyl alcohol. From a viewpoint that the desired product should be obtained in a high yield and under a high selectivity, the epoxidation step is preferably conducted in the presence of a catalyst containing a titanium-containing silicon oxide. The catalyst is preferably a catalyst containing titanium chemically bound to silicon oxide, so-called titanium-silica catalyst. Examples may include products in which a titanium compound is supported on a silica carrier, products in which a titanium compound is compounded with a silicon oxide by a co-precipitation or sol-gel method, titanium-containing zeolite compounds and the like.

In the present invention, isopropylbenzene hydroperoxide used as the raw material for the epoxidation step may be a dilute or thick purification or non-purification product.

The epoxidation reaction is carried out by contacting propylene and isopropylbenzene hydroperoxide with a catalyst. The reaction may be conducted in a liquid phase using a solvent. The solvent must be a liquid under the reaction temperature and pressure, and substantially inert to the reactants and the product. The solvent may be composed of a substance existing in a solution of the hydroperoxide used. When, for example, isopropylbenzene hydroperoxide is a mixture with isopropylbenzene as the raw material, it is also possible to use said material, without adding a solvent in particular, as the solvent. Other useful solvents include aromatic single-ring compounds (for example, benzene, toluene, chlorobenzene and o-dichlorobenzene), alkane (for example, octane, decane and dodecane) and the like. The epoxidation temperature is generally 0 to 200° C. and preferably 25 to 200° C. The pressure may be any pressure sufficient to keep liquid state of the reaction mixture. Generally, the pressure is advantageously 100 to 10,000 kPa.

The epoxidation can advantageously be carried out with a catalyst in the form of a slurry or a fixed-bed. The fixed-bed is preferred in the case of a large-scale industrial operation. In addition, the reaction can be carried out by a batch process, a semi-continuous process, a continuous process or the like. When a liquid containing the raw materials for reaction is passed through a fixed-bed, the catalyst is not contained at all or substantially in a liquid mixture discharged from a reaction zone.

The hydrogenolysis step in the present invention is a step in which cumyl alcohol obtained in the epoxidation step is subjected to hydrogenolysis to obtain isopropylbenzene, and said isopropylbenzene is recycled to the oxidation step as the raw material for the oxidation step. In other words, the same product, i.e. isopropylbenzene, used in the oxidation step is recovered. The hydrogenolysis is usually carried out by contacting cumyl alcohol and hydrogen with a catalyst. Any catalyst having a hydrogenation ability can be used as the catalyst. Examples of the catalyst include metal catalysts of metals of the group 8th to 10th such as those of cobalt, nickel, palladium and the like and metal catalysts of metals of the group 11th or 12th metals such as those of copper, zinc and the like. Copper catalysts are preferred from the viewpoint that by-products are suppressed. The copper catalysts include copper, Raney copper, copper-chromium, copper-zinc, copper-chromium-zinc, copper-silica, copper-alumina and the like. The reaction can be conducted in a liquid phase using a solvent or in a gaseous phase. The solvent must be substantially inert to the reactants and the product. The solvent may comprise a substance existing in a solution of the cumyl alcohol used. When, for example, cumyl alcohol is a mixture with isopropylbenzene as the product, it is possible to use this, without adding a solvent in particular, as the solvent. Other useful solvents include alkane (for example, octane, decane and dodecane), aromatic single-ring compounds (for example, benzene, ethylbenzene and toluene), and others. The temperature for the hydrogenolysis reaction is generally 0 to 500° C. and preferably 30 to 400° C. Generally, the pressure is advantageously 100 to 10,000 kPa. The hydrogenolysis can advantageously be carried out with a catalyst in the form of a slurry or a fixed-bed. The process of the present invention can be carried out by a batch process, a semi-continuous process or a continuous process. When a solution or a gas containing the raw materials for reaction is passed through a fixed-bed, the catalyst is not contained at all or substantially in a liquid mixture discharged from the reaction zone.

The greatest feature of the present invention is that isopropylbenzene hydroperoxide supplied to an epoxidation step has not undergone a heat history including heating at a temperature not lower than the temperature (t° C.) represented by the following equation (1), $$t(°C.)=150-0.8\times W \quad (1)$$

W: content (% by weight) of isopropylbenzene hydroperoxide in a solution containing isopropylbenzene hydroperoxide. When the condition described above is not satisfied, there are raised problems that a poisoned substance against the catalyst used for an epoxidation to obtain propylene oxide from propylene, is formed and thus the yield of epoxidation decreases together with lowering of the yield due to undergoing of heat decomposition of isopropylbenzene hydroperoxide. As a place where there is a possibility that isopropylbenzene hydroperoxide supplied to the epoxidation step undergoes the heat history, the oxidation step is illustrated. Further, when a concentration step and purification step are installed after the oxidation step, these steps can be listed as the step where it undergoes the heat history.

W in the equation (1) is a content(% by weight) of isopropylbenzene hydroperoxide in the solution containing isopropylbenzene hydroperoxide, and the content is preferably 5 to 80% by weight. When the content is too low, the industrial productivity is disadvantageously low. On the other hand, when the content is too large, decomposition easily proceeds, and the yield decreases, and, further dangerousness of a runaway reaction becomes high.

Still further, in the present invention, a concentration of an organic acid of the solution containing isopropylbenzene hydroperoxide to be supplied to the epoxidation step is preferably 0.5% by weight or less, more preferably 0.1% by weight or less. By specifying within this range, the activity of the catalyst used in the epoxidation step can be maintained at a high level and the life of the catalyst can be kept for longer time.

Furthermore, in the present invention, the concentration of sodium of the solution containing isopropylbenzene hydroperoxide to be supplied to the epoxidation step is preferably 0.1% by weight or less.

By specifying within this range, the activity of the catalyst used in the epoxidation step can be maintained at a high level and the life of the catalyst can be kept for longer time.

Moreover, in the present invention, the concentration of water of the solution containing isopropylbenzene hydroperoxide to be supplied to the epoxidation step is preferably 1% by weight or less.

By specifying within this range, the activity of the catalyst used in the epoxidation step can be maintained at high level, the life of the catalyst can be kept for longer time, and further, the epoxidation yield can be maintained higher.

EXAMPLE 1

An isopropyl benzene solution containing 20% by weight of isopropylbenzene hydroperoxide is heated to 120° C. ($<t=150-0.8\times20=134°$ C.) for 30 minutes. In this case, isopropylbenzene hydroperoxide heat-decomposed becomes 2.6% of the total.

Comparative Example 1

An isopropyl benzene solution containing 20% by weight of isopropylbenzene hydroperoxide is heated to 140° C. ($<t=150-0.8\times20=134°$ C.) for 30 minutes. In this case, isopropylbenzene hydroperoxide heat-decomposed amounts to 23.5% of the total, and the yield in the epoxidation step lowers because organic acids and heavy components in larger amounts as compared to Example 1 are produced.

EXAMPLE 2

An isopropyl benzene solution containing 50% by weight of isopropylbenzene hydroperoxide is heated to 100° C. ($<t=150-0.8\times50=110°$ C.) for 30 minutes. In this case, isopropylbenzene hydroperoxide heat-decomposed becomes 2.0% of the total.

Comparative Example 2

An isopropyl benzene solution containing 50% by weight of isopropylbenzene hydroperoxide is heated to 120° C. ($<t=150-0.8\times50=110°$ C.) for 30 minutes. In this case, isopropylbenzene hydroperoxide heat-decomposed amounts to 20.0% of the total, and the yield in the epoxidation step lowers because organic acids and heavy components in larger amounts as compared to Example 1 are produced.

Industrial Applicability

As described above, according to the present invention, there can be provided a process for producing propylene oxide, said process having excellent characteristics that propylene is converted to propylene oxide using isopropylbenzene hydroperoxide obtained from isopropylbenzene, as an oxygen carrier, that said isopropylbenzene can be repeatedly used, and that the activity of a catalyst used for epoxidation to obtain propylene oxide from propylene, can be maintained at a high level for long time.

What is claimed is:

1. A process for producing propylene oxide, which comprises steps described below, wherein isopropylbenzene hydroperoxide supplied to an epoxidation step has not undergone a heat history including heating at a temperature not lower than the temperature ($t°$ C.) represented by the following equation (1), $$t(° C.)=150-0.8\times W \qquad (1)$$

W: content (% by weight) of isopropylbenzene hydroperoxide in a solution containing isopropylbenzene hydroperoxide:

oxidation step; a step in which isopropylbenzene is oxidized to obtain isopropylbenzene hydroperoxide, epoxidation step; a step in which isopropylbenzene hydroperoxide obtained in the oxidation step is reacted with propylene to obtain propylene oxide and cumyl alcohol, and hydrogenolysis step; a step in which cumyl alcohol obtained in the epoxidation step is subjected to hydrogenolysis to obtain isopropylbenzene, and said isopropylbenzene is recycled to the oxidation step as a raw material for the oxidation step.

2. The process according to claim 1, wherein w in the equation (1) is 5 to 80% by weight.

* * * * *